(12) United States Patent
Xu et al.

(10) Patent No.: US 11,090,272 B2
(45) Date of Patent: Aug. 17, 2021

(54) LURASIDONE SOLID DISPERSION AND PREPARATION METHOD THEREOF

(71) Applicant: SUNSHINE LAKE PHARMA CO., LTD., Guangdong (CN)

(72) Inventors: Yuzhen Xu, Dongguan (CN); Ning Tian, Dongguan (CN); Xin Huang, Dongguan (CN); Jinsong You, Dongguan (CN); Fangfang Huang, Dongguan (CN)

(73) Assignee: Sunshine Lake Pharma Co., Ltd., Guangdong (CN)

( * ) Notice: Subject to any disclaimer, the term of this patent is extended or adjusted under 35 U.S.C. 154(b) by 0 days.

(21) Appl. No.: 16/474,601

(22) PCT Filed: Jan. 4, 2018

(86) PCT No.: PCT/CN2018/071326
§ 371 (c)(1),
(2) Date: Jun. 28, 2019

(87) PCT Pub. No.: WO2018/127088
PCT Pub. Date: Jul. 12, 2018

(65) Prior Publication Data
US 2019/0321304 A1  Oct. 24, 2019

(30) Foreign Application Priority Data
Jan. 6, 2017  (CN) .......................... 201710009826.8

(51) Int. Cl.
*A61K 9/48* (2006.01)
*A61K 31/496* (2006.01)

(52) U.S. Cl.
CPC .......... *A61K 9/4866* (2013.01); *A61K 9/4833* (2013.01); *A61K 9/4858* (2013.01); *A61K 9/4891* (2013.01); *A61K 31/496* (2013.01)

(58) Field of Classification Search
CPC .......... A61K 9/10; A61K 47/00; A61K 47/06; A61K 47/32; A61K 47/34; A61K 47/36;
(Continued)

(56) References Cited

U.S. PATENT DOCUMENTS

| 5,532,372 A | 7/1996 | Saji et al. |
| 2008/0274194 A1* | 11/2008 | Miller ................... A61K 31/58 424/489 |

(Continued)

FOREIGN PATENT DOCUMENTS

| CN | 102078309 A | 6/2011 |
| CN | 103006661 A | 4/2013 |

(Continued)

OTHER PUBLICATIONS

International Search Report of PCT/CN2018/071326.
Written Opinion of PCT/CN2018/071326.

*Primary Examiner* — Lakshmi S Channavajjala
(74) *Attorney, Agent, or Firm* — Kam Wah Law (57) ABSTRACT

It relates to a lurasidone solid dispersion and a preparation method, wherein the method comprises melting treatment of a mixture containing lurasidone, a medicinal hot melt carrier, optionally an acidic regulator and plasticizer in order to obtain the solid dispersion described herein, and wherein the lurasidone is provided in a form of free base. The lurasidone solid dispersion obtained by the preparation method according to the example of the invention has the characteristics of high dissolution rate (dissolution rate can reach 30%-70%) in a partial neutral medium (e.g. pH6.0). The bioavailability of lurasidone solid dispersion increased significantly and the food effect of lurasidone solid dispersion prepared from the example decreased remarkably. It overcomes the limitation of too many medication in the prior art and avoids the reduction of curative effect of the improper medication for (Continued)

the patient or even invalid, ensures the normal efficacy, thereby increases the patient's medication flexibility and compliance.

21 Claims, 3 Drawing Sheets

(58) Field of Classification Search
CPC ........ A61K 47/38; A61K 47/40; A61K 47/42; A61K 9/4866; A61K 9/2054; A61K 31/496
See application file for complete search history.

(56) References Cited

U.S. PATENT DOCUMENTS

| | | | | |
|---|---|---|---|---|
| 2011/0028456 | A1* | 2/2011 | Lulla ...................... | A61K 9/146 514/220 |
| 2013/0143867 | A1* | 6/2013 | Fogel ................... | A61K 31/185 514/211.13 |
| 2014/0343076 | A1* | 11/2014 | Kulkarni .............. | A61K 31/496 514/254.04 |
| 2015/0157628 | A1 | 6/2015 | Kannusamy et al. | |

FOREIGN PATENT DOCUMENTS

| | | | | |
|---|---|---|---|---|
| CN | 104971046 | A | | 10/2015 |
| CN | 105395493 | A * | 3/2016 | ........... A61K 31/496 |
| CN | 105395493 | A | | 3/2016 |
| CN | 106539769 | A | | 3/2017 |
| CN | 105395493 | B * | 2/2018 | |
| WO | 2014076712 | A2 | | 5/2014 |

* cited by examiner

LURASIDONE SOLID DISPERSION AND PREPARATION METHOD THEREOF

CROSS REFERENCE TO RELATED APPLICATIONS

This is a U.S. national stage application of the International Patent Application No. PCT/CN2018/071326, filed Jan. 4, 2018, which claims priority to Chinese Patent Application No. 201710009826.8, filed Jan. 6, 2017, both of which are incorporated herein by reference in their entirety.

FIELD

The invention relates to the field of pharmaceutical. In particular, the invention relates to a lurasidone solid dispersion, a preparation method for preparing the lurasidone solid dispersion, a pharmaceutical composition, a pharmaceutical combination and use of the pharmaceutical composition in the preparation of a medicament.

BACKGROUND

Lurasidone hydrochloride is an atypical antipsychotic drug. On Oct. 28, 2010, the U.S. Food and Drug Administration (FDA) approved lurasidone hydrochloride tablets, which are developed by Dainippon Sumitomo Pharma Co., Ltd., with the trade name of Latuda, respectively 20 mg, 40 mg, 60 mg, 80 mg, 120 mg/tablet, for the treatment of schizophrenia. On Jun. 28, 2013, the FDA approved two new indications for the use of lurasidone as 1) monotherapy and 2) adjunctive therapy with lithium or sodium valproate used for treating type I bipolar affective disorder in adult patients.

The mechanism of lurasidone action is not yet clear. It has been suggested that use of lurasidone for the treatment of schizophrenia has significant efficacy for both positive and negative symptoms in psychotic patients, primarily through acting on central type 2 dopamine (D2) receptor and type 2 serotonin (5-HT2A) receptor, etc. In addition, lurasidone can also improve cognitive function. And lurasidone causes less weight gain without causing changes in glucose, lipid (lipoid), ECG and QT intervals.

However, currently available lurasidone tablets have low bioavailability, and must be administered with food at the same time. The food must have calories greater than 350 calories, otherwise the peak plasma concentration ($C_{max}$) of lurasidone and the area under the curve of drug concentration-time (AUC) respectively decrease 3-fold and 2-fold, even though the bioavailability is only 9%-19%. The administration requirements of lurasidone for schizophrenia patients and depressed patients are more stringent, usually the calories of normal diet are not be strictly calculated, and some patients refuse to eat or loss of appetite symptoms; if the patients don't eat enough food for drug administration, it may lead to the decrease of the bioavailability of the drug, affect the efficacy, delay the patient's condition.

Therefore, the development of a dosage form that can reduce or eliminate food effects to improve patient compliance is a key issue to be solved by drug developers.

SUMMARY

This application is based on the inventor's discovery of the following issues and facts.

The solubility of existing lurasidone hydrochloride has a strong pH-dependent, and is higher in water and partial acidic medium; but the solubility declines rapidly in the neutral medium. A large amount of the lurasidone dissolved or partially dissolved in the stomach is precipitated out while entering the intestinal neutral pH environment, and only a small part of the lurasidone is dissolved and absorbed, thus resulting in lower bioavailability. At the same time, due to the small amount of drug dissolved and absorbed in the intestine, the food-induced gastrointestinal surfactant is further increased to solubilize the food, resulting in excessive food effect. Therefore, the inventors believe that it is possible to reduce its food effect if a greater solubilization of lurasidone is possible. Based on the above, the present invention provides a method of preparing a lurasidone solid dispersion. The lurasidone solid dispersion prepared by the method greatly increases the dissolution of lurasidone in the intestinal tract and greatly reduces the food effect.

In the first aspect, the invention provides a lurasidone solid dispersion. According to the examples of the invention, the lurasidone solid dispersion comprises lurasidone, a medicinal hot melt carrier and an acidic regulator, wherein the lurasidone is provided in a form of free base. Surprisingly, the inventors have found that the lurasidone provided in a form of free base as a breakthrough greatly reduces the melting point of the lurasidone solid dispersion, and the acidic regulator contained in the lurasidone solid dispersion increases the dissolution of lurasidone in the partial neutral medium.

The lurasidone solid dispersion prepared from the example of the present invention is particularly suitable for obtaining by melting treatment.

According to the example of the present invention, the lurasidone solid dispersion described above further comprises at least one of the following additional technical features.

According to the example of the present invention, a weight ratio of the lurasidone to the medicinal hot melt carrier is ranged from about 1:1 to about 1:50. The inventor found that the weight ratio of the lurasidone to the medicinal hot melt carrier is less than 1:50 will result in a too high proportion of the medicinal hot melt carrier, and the weight or volume of the unit dosage formulation is too large to satisfy the normal dosing requirements, resulting in patient's medication compliance deteriorating; the weight ratio of the lurasidone to the medicinal hot melt carrier is more than 1:1 will result in that the proportion of medicinal hot melt carrier is too low, the dispersity of the drug may be poor, and the quality of the resulting solid dispersion is affected, the solubilization effect is reduced.

According to the example of the present invention, a weight ratio of the lurasidone to the medicinal hot melt carrier is ranged from about 1:1 to about 1:30. The inventor found that when the weight ratio of the lurasidone to the medicinal hot melt carrier is ranged from 1:1 to 1:30, the weight of the unit dosage formulation is suitable, the dispersity of the drug is better, and the solubilization effect is better.

According to the example of the present invention, a weight ratio of the lurasidone to the medicinal hot melt carrier is ranged from about 1:3 to about 1:30. The inventor found that when the weight ratio of the lurasidone to the medicinal hot melt carrier is ranged from 1:3 to 1:30, the weight of a unit dosage formulation is suitable, the dispersity of the drug is better, and the solubilization effect is better.

The type of the medicinal hot melt carrier is not particularly limited. According to the specific example of the present invention, the medicinal hot melt carrier comprises at least one of povidone, copovidone, polyvinyl caprolactam-polyvinyl acetate-polyethylene glycol graft copolymer (soluplus), a hydroxypropyl methyl cellulose acetate succinate (HPMCAS), a polyethylene glycol, a hydroxypropyl methyl cellulose (HPMC), hydroxypropyl cellulose, an ethyl cellulose and an acrylic resin (e.g. Eudragit E, Eudragit L). The medicinal hot-melt carrier described above can make the drug highly dispersed, and the drug has good thermal stability and thermoplasticity, which is beneficial for hot melt extrusion process, and can also inhibit the formation and growth of drug crystal nucleus, thus increasing the dissolution of lurasidone.

According to the example of the present invention, a weight ratio of the lurasidone to the acidic modulator is ranged from about 1:0.05 to about 1:25. The inventor found that the weight ratio of the lurasidone to the acidic modulator is higher than 1:0.05 will result in a too low proportion of the acidic modulator and poor dissolution of the drug; while the weight ratio of the lurasidone to the acidic regulator is less than 1:25 will result in a too high proportion of acidic regulator, and then lead to the weight or volume of a unit dosage formulation is too large to meet the normal dosing requirements, the patient's medication compliance becomes poor, and the hot melting process may be affected.

According to the example of the present invention, a weight ratio of the lurasidone to the acidic modulator is ranged from about 1:1 to about 1:20. The inventor found that in this case the weight or volume of a unit dosage formulation is more suitable, the dissolution of drug is increased, and the hot melting process is more smooth.

According to the example of the present invention, the acidic regulator described herein comprises at least one of citric acid monohydrate, anhydrous citric acid, fumaric acid, malic acid, succinic acid, ascorbic acid, tartaric acid, sorbic acid and glycine. The acidic regulator described above can effectively improve the dissolution of lurasidone in the partial neutral medium, and lurasidone and acidic regulator can be mixed effectively during the mixing and hot melt extrusion. During the process of dissolution, both of them are dissolved out at the same time, and acidic regulator can adjust the pH value of the microenvironment around the drug which is beneficial for the dissolution of lurasidone.

According to the example of the present invention, the lurasidone solid dispersion described herein further comprises a plasticizer. It is found that plasticizer can improve the feasibility of hot melting process and reduce the hot melting temperature and the torque of hot melting process. The solubility of the lurasidone in lurasidone solid dispersion in the partial neutral medium can be further improved.

According to the example of the present invention, a weight ratio of lurasidone to the plasticizer is ranged from about 1:0 to about 1:10. The inventor found that when the weight ratio of the lurasidone to the plasticizer is less than 1:10, the extrusion process is affected and the granulation characteristics of the extrudate are affected, making the extrudate difficult to smash and granulate. At the same time, the weight or volume of a unit dosage formulation is too large to meet the normal dosing requirements, the patient's medication compliance becomes poor.

According to the example of the present invention, a weight ratio of lurasidone to the plasticizer is about 1:0.5 to about 1:5. The inventor found that in this case the weight or volume of a unit dosage formulation is suitable and the hot melting process is smooth.

According to the example of the present invention, the plasticizer described herein comprises at least one of a poloxamer, a polyethylene glycol, triethyl citrate, diethyl phthalate and glycerol monostearate. The inventor found that the addition of the plasticizer described above can reduce the processing temperature of the polymer extrusion process, improve the feasibility of the process, reduce the torque of the hot melting process, and at the same time, the plasticizer still has some solubilizing effect.

In another aspect, the invention provides a method of preparing lurasidone solid dispersion. According to the example of the present invention, the method described herein comprises melting treatment that is melting and mixing a mixture containing lurasidone and a medicinal hot melt carrier; and cooling the mixture to give the lurasidone solid dispersion, wherein the lurasidone is in a form of free base.

In another aspect, the invention provides a method of preparing lurasidone solid dispersion. According to the example of the present invention, the method described herein comprises melting treatment that is melting and mixing a mixture containing lurasidone, a medicinal hot melt carrier, an acidic regulator, and optionally a plasticizer; and cooling the mixture to give the lurasidone solid dispersion, wherein the lurasidone is provided in a form of free base. The method of preparing the lurasidone solid dispersion according to the example of the present invention has less process steps without solvent and with simple operation, and is suitable for continuous production, has high yield and is easy to achieve industrial production. More importantly, the lurasidone solid dispersion obtained by the preparation method according to the example of the invention has the characteristics of high dissolution rate (dissolution rate can reach 30%-70%) in a partial neutral medium (e.g., pH 6.0). The bioavailability of lurasidone solid dispersion is significantly increased and the food effect of lurasidone solid dispersion prepared from the example of the present invention is remarkably decreased, overcoming the limitation of medication in the prior art and avoiding the curative effect of the improper medication of the patient or even invalid, to ensure the normal efficacy, thereby increasing the patient's medication flexibility and compliance.

According to the example of the present invention, the lurasidone solid dispersion described above further comprises at least one of the following additional technical features.

According to the example of the present invention, the melting and mixing step is carried out in a hot melt extruder. The hot melt extruder is suitable for continuous production, has high yield and is easy to achieve industrial production.

According to the example of the present invention, a weight ratio of lurasidone to the medicinal hot melt carrier is ranged from about 1:1 to about 1:50. The inventor found that the weight ratio of the lurasidone to the medicinal hot melt carrier is less than 1:50 will result in a too high proportion of the medicinal hot melt carrier, and the weight or volume of a unit dosage formulation is too large to satisfy the normal dosing requirements which results in patient's medication compliance deteriorating; while the weight ratio of lurasidone to the medicinal hot melt carrier is more than 1:1 will result in that the proportion of medicinal hot melt carrier is too low, the dispersity of the drug may be poor, and the quality of the resulting solid dispersion is affected, the solubilization effect is reduced.

The type of the medicinal hot melt carrier is not particularly limited. According to the specific example of the present invention, the medicinal hot melt carrier comprises at least one of povidone, copovidone, polyvinyl caprolactam-polyvinyl acetate-polyethylene glycol graft copolymer (soluplus), a hydroxypropyl methyl cellulose acetate succinate (HPMCAS), a polyethylene glycol, a hydroxypropyl methyl cellulose, hydroxypropyl cellulose, an ethyl cellulose and an acrylic resin. The inventor found that the medicinal hot-melt carrier described above can make the drug highly dispersed, and the drug has good thermal stability and thermoplasticity, which is beneficial for hot melt extrusion process, and can also inhibit the formation and growth of drug crystal nucleus, thus increasing the dissolution of lurasidone.

According to the example of the present invention, a weight ratio of lurasidone to the the acidic modulator—is ranged from about 1:0.05 to about 1:25. The inventor found that the weight ratio of lurasidone to the acidic modulator is higher than 1:0.05 will result in a too low proportion of the acidic modulator and poor dissolution of the drug; while the weight ratio of the lurasidone to the acidic regulator is less than 1:25 will result in a too high proportion of acidic regulator, and then lead to the weight or volume of a unit dosage formulation is too large to meet the normal dosing requirements, the patient's medication compliance becomes poor, and the hot melting process may be affected. According to the example of the present invention, the acidic regulator described herein comprises at least one of citric acid monohydrate, anhydrous citric acid, fumaric acid, malic acid, succinic acid, ascorbic acid, tartaric acid, sorbic acid and glycine. The acidic regulator described above can effectively improve the dissolution of lurasidone in the partial neutral medium, and the inventor found that lurasidone and acidic regulator can be mixed effectively during the mixing and hot melt extrusion. During the process of dissolution, both of them are dissolved out at the same time, acidic regulator can adjust the pH value of the microenvironment around the drug which is beneficial for the dissolution of lurasidone.

According to the example of the present invention, the mixture described herein further comprises a plasticizer. The inventor found that plasticizer can improve the feasibility of hot melting process and reduce the hot melting temperature and the torque of hot melting process. The solubility of the lurasidone in lurasidone solid dispersion in the partial neutral medium can be further improved.

According to the example of the present invention, a weight ratio of lurasidone to the plasticizer is ranged from about 1:0 to about 1:10. The inventor found that when the weight ratio of the lurasidone and the plasticizer is less than 1:10, the extrusion process is affected and the granulation characteristics of the extrudate are affected, making the extrudate difficult to granulate; at the same time, the weight or volume of the unit dose preparation is too large to meet the normal dosing requirements and the patient's medication compliance becomes poor.

According to the example of the present invention, the plasticizer described herein comprises at least one of a poloxamer, a polyethylene glycol, triethyl citrate, diethyl phthalate and glycerol monostearate. The inventor found that the addition of the plasticizer described above can reduce the processing temperature of the polymer extrusion process, improve the feasibility of the process, reduce the torque of the hot melting process, and at the same time, the plasticizer still has some solubilizing effect.

According to the example of the present invention, the melting and mixing step in melting treatment is carried out at a temperature from about 80° C. to about 200° C. while the screw speed of the hot melt extruder is from about 30 rpm to about 1000 rpm. The temperature and screw speed of the hot melt extruder are selected based on the type of medicinal hot melt carrier employed. The melting and mixing step is carried out at a temperature from about 80° C. to about 200° C. while the screw speed of the hot melt extruder is from about 30 rpm to about 1000 rpm to extrude the target mixture smoothly, and the extrusion speed and the yield can meet the requirements, and the solubilization effect is good.

According to the example of the present invention, the melting and mixing step in melting treatment is carried out at a temperature from about 115° C. to about 175° C. while the screw speed of the hot melt extruder is from about 30 rpm to about 300 rpm. The temperature and screw speed of the hot melt extruder are selected based on the type of medicinal hot melt carrier employed. The melting and mixing step is carried out at a temperature from about 115° C. to about 175° C. while the screw speed of the hot melt extruder is from about 30 rpm to about 300 rpm to extrude the target mixture smoothly, and the extrusion speed and the yield can meet the requirements, and the solubilization effect is better.

According to the example of the present invention, a lurasidone solid dispersion prepared by the method described above. The inventors found that the lurasidone solid dispersion is remarkably improved the dissolution of lurasidone in the partial neutral medium, is remarkably increased the bioavailability and is remarkably decreased the food effect.

In the third aspect, the invention provides a pharmaceutical composition. According to the example of the present invention, the pharmaceutical composition disclosed herein comprises the lurasidone solid dispersion described above or prepared from the method described above. The pharmaceutical composition according to the example of the present invention is advantageous to the absorption of lurasidone and can ensure the increase of lurasidone dissolution in the small intestine without considering the influence of food on the absorption of lurasidone, reduces the excessive medication restrictions and avoids reduced efficacy due to improper medication or even invalid, to ensure the normal efficacy of drug, thereby increasing the patient's medication flexibility and compliance.

According to the example of the present invention, the pharmaceutical composition described above further comprises at least one of the following additional technical features.

According to the example of the present invention, the pharmaceutical composition disclosed herein further comprises a pharmaceutically acceptable excipient. The pharmaceutically acceptable excipient can make the pharmaceutical composition present a certain dosage form, which is beneficial to the patient for taking or injecting to improve the bioavailability and stability of the drug.

According to the example of the present invention, the pharmaceutically acceptable excipient comprises at least one of a filler, a disintegrant, an adhesive, a surfactant, a flavoring agent and a lubricant.

Wherein, the selection of filler, disintegrant, adhesive, surfactant, flavoring agent and lubricant is not particularly limited. According to the example of the present invention, the filler comprises at least one of lactose, starch, microcrystalline cellulose, mannitol, dextrin, pregelatinized starch, corn starch, sorbitol, calcium sulfate, calcium hydrogen phosphate and calcium carbonate. According to the specific example of the present invention, the disintegrant described herein comprises at least one of crospovidone, croscarmellose sodium, sodium starch glycolate, dry starch, low-substituted hydroxypropyl cellulose. According to the specific example of the present invention, the adhesive described herein comprises at least one of starch, pregelatinized starch, sodium carboxymethylcellulose, hydroxypropylcellulose, methylcellulose, ethylcellulose, a hypromellose, sucrose, gelatin, polyvinylpyrrolidone, microcrystalline cellulose and copovidone. According to the specific example of the present invention, the surfactant described herein comprises at least one of sodium lauryl sulfate, quaternary ammonium compound, lecithin, glycerol fatty acid ester, sorbitan fatty acid ester and polysorbate. According to the specific example of the present invention, the flavoring agent described herein comprises at least one of sucrose, sucralose, acesulfame, aspartame, stevioside, sodium saccharin and sodium cyclamate. According to the example of the present invention, the lubricant described herein comprises at least one of magnesium stearate, powdered silica, stearic acid, talc, docosanoic acid glycerol ester, hydrogenated castor oil, sodium stearyl fumarate.

The addition of filler can improve the properties of the material, adjust the compressibility and fluidity, improve the product performance and facilitate the formation of the preparation form, so that the preparation process is more smooth; the addition of disintegrant can make the tablets rapidly disintegrate in the body, so that the drug can be dissolved and absorbed rapidly; the adhesive has a certain viscosity that can make some loose powder form particles having certain size, improve fluidity, and can adjust the disintegration of the composition and the release of drug in a certain degree; the addition of surfactant can help the dispersion of the drug, and can improve solubilization in a certain degree; the addition of flavoring agent in specific dosage forms such as orally disintegrating tablets or suspensions can improve the taste of drugs, shield the bad smell of drugs, improve patient's compliance; the addition of lubricant can reduce the friction between the particles or between the tablets and the die, that makes the pressure equally distribute during the process of tableting, and it is easier for tableting.

According to the example of the present invention, the pharmaceutical composition is in the form of granule, tablet, capsule or enteric formulation. As described above, the dissolution of the pharmaceutical composition according to the example of the present invention in the small intestine is significantly increased. The pharmaceutical composition of the example of the present invention is in a form of a granule, a tablet, a capsule or an enteric-coated preparation. The characteristics of the composition adapted to the example of the present invention help to further improve the bioavailability of the pharmaceutical composition.

In the fourth aspect, the invention provides a pharmaceutical combination, wherein the pharmaceutical combination is used for treating or preventing a mental disease, for example, schizophrenia, bipolar I disorder, autism, bipolar disorder and depression. According to the example of the present invention, the pharmaceutical combination disclosed herein comprises: lurasidone used as a first active agent, wherein the lurasidone exists in the form of lurasidone solid dispersion described above or prepared by the method described above; a medicament different from lurasidone used as a second active agent, wherein the medicament is used for treating or preventing a mental disease. According to the pharmaceutical combination of example in the present invention, the effect of treating or preventing of psychiatric disease is remarkable, and the flexibility and compliance of the patient's medication are remarkably improved.

The invention provides the use of the lurasidone solid dispersion or the pharmaceutical composition described above in the manufacture of a medicament, wherein the medicament is used for treating or preventing a mental disease, for example, schizophrenia, bipolar I disorder, autism, bipolar disorder and depression. As described above, the pharmaceutical composition provided in the present application has the characteristics of high dissolution rate and high bioavailability in a partial neutral medium. The pharmaceutical composition provided in the present application can effectively treat or prevent mental disease such as schizophrenia and has low food effect, avoids the side effects of curative effect reduction or even invalid caused by improper medication administration so as to ensure the normal efficacy of the drug.

In the fifth aspect, the invention provides a method of treating or preventing a mental disease in a patient, for example, schizophrenia, bipolar I disorder, autism, bipolar disorder and depression, by administering to the patient a therapeutically effective amount of the lurasidone solid dispersion or pharmaceutical composition described above.

As used herein, all numbers disclosed herein are approximate values, regardless whether the word "about" is used in connection therewith, which means within 5% and particularly within 1% of a given value or range. Alternatively, the term "about" means within an acceptable standard error range of the mean, when considered by one of the ordinary skill in the art. Therefore, whenever a number having a value N is disclosed, any number having the value N+/−1%, N+/−2%, N+/−3%, N+/−4% or N+/−5% is specifically disclosed, wherein "+/−" refers to plus or minus.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a excipient" means one or more excipients, and thus, possibly, more than one excipient is contemplated and may be employed or used in an implementation of the described embodiments.

DESCRIPTION OF THE PREFERRED EMBODIMENTS

The examples of the present invention are described in detail below. The examples described below are exemplary, and are only used to explain the present invention, but should not be construed as limiting the present invention. Specific techniques or conditions which are not specified in the examples, can accord to the techniques or conditions described in the literature, or accord to the product specifications. Reagents or instruments used, the manufacturer of which are not specified, are conventional products purchased from the market.

Among them, the reference formulation used in the examples was 40 mg lurasidone hydrochloride tablet which was prepared by Sumitomo.

Lurasidone used in the examples was in a form of free base, unless otherwise indicated herein or clearly contradicted by the context.

In an earlier study, the inventor found that the reference formulation (lurasidone hydrochloride tablet, 40 mg, Sumitomo) can be 100% dissolved in the mixture of 0.1 M hydrochloric acid and pH 3.8 medium, but the bioavailability of the reference formulation after eating is only 9%-19%, and the bioavailability in animals is less than 12%; it can be seen that these two mediums can only represent the stomach environment of fasting or part of the human stomach environment under the state of feeding, but can not represent the environment of small intestine site. However, the main part of the absorption of lurasidone is mainly in the small intestine, and the solubility of lurasidone has a strong pH-dependent. The solubility in water and a partial acidic medium is better, and the solubility in neutral medium decreases rapidly. Therefore, uses of these two medium (0.1 M hydrochloric acid and pH 3.8 medium) respectively can not represent the state of the drug in the body.

The pH value in the upper part of the small intestine is about 6.0, so during the study, the inventor first chose 6.0 as the pH value of the dissolution medium, whereas under the fasted and fed conditions, small bowel can secrete different concentrations of bile salts, i.e., a certain amount of surfactant is present. Therefore, the inventor investigated the dissolution of reference formulation in the pH 6.0 medium with adding different concentrations of surfactant (sodium lauryl sulfate), and found that the dissolution platform of reference formulation at pH 6.0 with adding 0.01% SDS (sodium lauryl sulfate) was close to the bioavailability of reference formulation under fasted condition, so the inventor chose pH 6.0 with adding 0.01% SDS as the dissolution screening medium of fasting; whereas the concentration of surfactant during eating condition is higher than the concentration of surfactant during fasting, so the inventor chose pH 6.0 with adding 0.03% SDS as the dissolution medium to judge the dissolution of the formulation under fed condition.

The inventor found that the patent application WO2014076712 A2 disclosed a method of preparing a lurasidone hydrochloride solid dispersion, which requires the use of a large amount of organic solvent, and found that the dissolution platform of the solid dispersion prepared according to the prescription and process was only 7% at pH 6.0 with adding 0.01% SDS, which is increased compared with the reference formulation, but the solubilization effect is far less than that of the prescription of the present application; patent application US20140343076A1 disclosed a composition of lurasidone hydrochloride comprising a mixture of lurasidone with at least one acid, at least one surfactant and other excipients, and the inventor found that the solubilization effect of the composition prepared according to the prescription and process is far less than that of the prescription of the present application; CN105395493A disclosed a lurasidone hydrochloride tablet prepared by a method of hot melting of potassium citrate and sorbitol, and then adding lurasidone hydrochloride with melting to extrude granulation, additionally adding excipient and pressing to give tablet. The method of the patent requires two-step melting, and it was found that the dissolution platform of the tablet prepared according to its prescription and process is also low at pH 6.0 with adding 0.01% SDS. All these contents are specifically described in detail in comparative examples 1 to 3.

Comparative Example 1 Patent Application US20140343076A1

The specific prescription in patent application US20140343076A1 is shown in Table 1.

TABLE 1

|  | Component | Percentage (%) |
|---|---|---|
| Additive | Lurasidone hydrochloride | 15.27 |
|  | Microcrystalline cellulose | 39.50 |
|  | Pregelatinized starch | 21.63 |
|  | Croscarmellose sodium | 16.54 |
| Granulating liquid | HPMC | 0.70 |
|  | Citric acid | 5.09 |
|  | Magnesium stearate | 1.27 |
|  | Total | 100.00 |

A certain amount of purified water which was 25% (W/W) of the weight of the total mixed powder was weighed, then HPMC and citric acid were weighed according to the prescription ratio to dissolve in the purified water as a granulating liquid for use.

Additives were weighed according to the prescription listed in table 1, and then mixed for 10 min as a granulating substrate.

Granulating liquid was added and granulation was performed using manual wet granulation, then wet granulations were screened through a 40 mesh screen and dried for 60 min in an oven at 50° C. Dried granulations were screened through a 40 mesh screen, then magnesium stearate was added additionally, mixed, and the resulting mixture was filled into capsules.

Comparative Example 2 Patent Application CN105395493A

The specific prescription in patent application CN105395493A is shown in Table 2.

TABLE 2

|  | Component | Percentage (%) |
|---|---|---|
| Component contained in the hot melt process | Lurasidone hydrochloride | 9.26 |
|  | Potassium citrate | 9.26 |
|  | Sorbitol | 27.78 |
| Additive | Calcium hydrophosphate | 50.93 |
|  | Colloidal silicon dioxide | 2.31 |
|  | Magnesium stearate | 0.46 |
|  | Total | 100.00 |

Potassium citrate and sorbitol were heat melted, then lurasidone hydrochloride was added into the mixture with melting; after the mixture was cooled, additives were added, and the resulting mixture was grinded, sieved and then filled into capsules.

Comparative Example 3 Patent Application WO2014076712A2

The specific prescription in patent application WO2014076712A2 is shown in Table 3.

TABLE 3

| Component | Percentage (%) |
|---|---|
| Lurasidone hydrochloride | 25.00 |
| Copovidone | 75.00 |
| Methanol | 100 mL (removed later) |
| Dichloromethane | 100 mL (removed later) |
| Total | 100.00 |

Lurasidone hydrochloride and copovidone were weighed according to the prescription, and then both of them were dissolved in a mixed solvent of methanol and dichloromethane at a volume ratio of 1:1 (200 mL in total) to dissolve the drug and carrier sufficiently. The resulting mixture was dried by spray drying at 60-65° C. to get dry spray powder, and then the dry spray powder was filled directly into capsules.

In addition, in order to facilitate the explanation of the problems, the inventors provide the following comparative examples 4 to 6, specifically as follows.

Comparative Example 4 Hot-Melt Powder without Adding Acidic Regulator

The specific prescription is shown in Table 4.

TABLE 4

| | Component | Percentage (%) |
|---|---|---|
| Component contained in the hot melt process | Lurasidone hydrochloride | 12.50 |
| | Copovidone VA64 | 62.50 |
| Additive | microcrystalline cellulose | 25.00 |
| | Total | 100.00 |

According to the prescription in table 4, components contained in the hot melt process were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 30 rpm. The resulting extrudate was cooled and crushed, then the crushed material was screened through 60 mesh sieve; additive microcrystalline cellulose was added, mixed, and the resulting mixture was filled into capsules.

Comparative Example 5

The specific prescription is shown in Table 5.

TABLE 5

| Component | Percentage (%) |
|---|---|
| Lurasidone | 10.64 |
| Soluplus | 53.21 |
| Citric acid monohydrate | 11.15 |
| Microcrystalline cellulose | 25.00 |
| Total | 100.00 |

The prescription is shown in Table 5. The components above were weighed, mixed directly and completely without melting treatment, and then filled into capsules.

Comparative Example 6

The specific prescription is shown in Table 6.

TABLE 6

| Component | Percentage (%) |
|---|---|
| Lurasidone hydrochloride | 10.75 |
| Soluplus | 53.77 |
| Citric acid monohydrate | 10.48 |
| Microcrystalline cellulose | 25.00 |
| Total | 100.00 |

The components above were weighed according to the prescription in table 6, mixed completely without melting treatment, and then filled into capsules.

In addition, in order to further illustrate the problem, the inventor also tried other comparative experiments, specifically: according to the prescription shown in table 5 or table 6, the components were mixed, granulated by wet granulation and then filled into capsules, or, the lurasidone, carrier and acidic regulator were dissolved in methanol and dried by spray drying, then the resulting mixture was filled into capsules.

The preparation examples of the present invention will be described in detail below. The preparation process of the pharmaceutical composition of the present invention is summarized as follows:

1. The lurasidone, medicinal hot-melt carrier, acidic regulator and, optionally, plasticizer are screened through a sieve and mixed thoroughly to give physical mixture;
2. The above mixture are added uniformly to a hot melting extruder and extruded at a suitable temperature and screw speed. After the material is sheared, extruded and mixed, the material is finally extruded in strips or sheets to obtain extrudates;
3. The extrudates is cooled, crushed and sieved to obtain the particles or powder of the lurasidone solid dispersion.
4. The particles or powder of lurasidone solid dispersion are mixed uniformly with pharmaceutically acceptable excipient to prepare oral pharmaceutical formulations, such as granules, tablets, capsules and the like. Also included are enteric formulations such as enteric-coated tablets, or enteric-coated capsules.

The specific preparation process is as described in examples 1 to 16.

Example 1

The specific prescription is shown in Table 7.

TABLE 7

| | Component | Percentage (%) |
|---|---|---|
| Component contained in the hot melt process | Lurasidone | 10.64 |
| | Copovidone VA64 | 53.21 |
| | Fumaric acid | 11.15 |
| Additive | Microcrystalline cellulose | 25.00 |
| | Total | 100.00 |

According to the prescription in table 7, components contained in the hot melt process were weighed, mixed completely, and added into the feeder of hot melt extruder to extrude by hot melting, while the temperature of barrel was set at 115° C., 135° C., 165° C., 165° C., 165° C., 165° C., 165° C., 160° C. and screw speed was set at 30 rpm. The resulting extrudate was cooled and crushed, then the crushed material was screened through 60 mesh sieve; additive microcrystalline cellulose was added according to the prescription, mixed and the resulting mixture was filled into capsules.

Example 2

According to the prescription and preparation process of example 1, the resulting granules were finally filled into the enteric capsule shells.

Example 3

The specific prescription is shown in Table 8.

TABLE 8

|  | Component | Percentage (%) |
|---|---|---|
| Component contained in the hot melt process | Lurasidone | 10.64 |
|  | Soluplus | 53.21 |
|  | Fumaric acid | 11.15 |
| Additive | Microcrystalline cellulose | 25.00 |
|  | Total | 100.00 |

According to the prescription in table 8, components contained in the hot melt process were weighed, mixed completely, and then added into the feeder of hot melt extruder to extrude by hot melting, while the temperature of barrel was set at 160° C., 165° C., 170° C., 170° C., 170° C., 170° C., 170° C., 165° C. and screw speed was set at 30 rpm. The resulting extrudate was cooled and crushed, then the crushed material was screened through 60 mesh sieve; additive microcrystalline cellulose was added according to the prescription, mixed, and the resulting mixture was filled into capsules.

Example 4

The specific prescription is shown in Table 9.

TABLE 9

|  | Component | Percentage (%) |
|---|---|---|
| Component contained in the hot melt process | Lurasidone | 10.64 |
|  | Soluplus | 53.21 |
|  | Citric acid monohydrate | 11.15 |
| Additive | Mannitol | 25.00 |
|  | Total | 100.00 |

According to the prescription in table 9, components contained in the hot melt process were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 200 rpm. The resulting extrudate was cooled and crushed, then the crushed material was screened through 60 mesh sieve; additive mannitol was added according to the prescription, mixed, and the resulting mixture was filled into capsules.

Example 5

The specific prescription is shown in Table 10.

TABLE 10

|  | Component | Percentage (%) |
|---|---|---|
| Component contained in the hot melt process | Lurasidone | 9.32 |
|  | Soluplus | 46.60 |
|  | Fumaric acid | 9.76 |
|  | Poloxamer | 9.32 |
| Additive | Mannitol | 25.00 |
|  | Total | 100.00 |

According to the prescription in table 10, components contained in the hot melt process were weighed, mixed completely, and then added into the feeder of hot melt extruder to extrude by hot melting, while the temperature of barrel was set at 115° C., 135° C., 150° C., 150° C., 150° C., 150° C., 150° C., 145° C. and screw speed was set at 30 rpm. The resulting extrudate was cooled and crushed, then the crushed material was screened through 60 mesh sieve; additive mannitol was added according to the prescription, mixed, and the resulting mixture was filled into capsules.

Example 6

The specific prescription is shown in Table 11.

TABLE 11

|  | Component | Percentage (%) |
|---|---|---|
| Component contained in the hot melt process | Lurasidone | 9.32 |
|  | Copovidone VA64 | 46.60 |
|  | fumaric acid | 9.76 |
|  | PEG 4000 | 9.32 |
| Additive | mannitol | 25.00 |
|  | Total | 100.00 |

According to the prescription in table 11, components contained in the hot melt process were weighed, mixed completely, and then added into the feeder of hot melt extruder to extrude by hot melting, while the temperature of barrel was set at 115° C., 135° C., 150° C., 150° C., 150° C., 150° C., 150° C., 145° C. and screw speed was set at 100 rpm. The resulting extrudate was cooled and crushed, then the crushed material was screened through 60 mesh sieve; additive mannitol was added according to the prescription, mixed, and the resulting mixture was filled into capsules.

Example 7

The specific prescription is shown in Table 12.

TABLE 12

|  | Component | Percentage (%) |
|---|---|---|
| Component contained in the hot melt process | Lurasidone | 10.64 |
|  | HPMCAS | 53.21 |
|  | Fumaric acid | 11.15 |
| Additive | Microcrystalline cellulose | 25.00 |
|  | Total | 100.00 |

According to the prescription in table 12, components contained in the hot melt process were weighed, mixed completely, and then added into the feeder of hot melt extruder to extrude by hot melting, while the temperature of barrel was set at 135° C., 150° C., 175° C., 175° C., 175° C., 175° C., 175° C., 170° C., and screw speed was set at 100 rpm. The resulting extrudate was cooled and crushed, then the crushed material was screened through 60 mesh sieve; additive microcrystalline cellulose was added according to the prescription, mixed, and the resulting mixture was filled into capsules.

Example 8

The specific prescription is shown in Table 13.

TABLE 13

|  | Component | Percentage (%) |
| --- | --- | --- |
| Component contained in the hot melt process | Lurasidone | 14.86 |
|  | Copovidone VA64 | 44.58 |
|  | Fumaric acid | 15.56 |
| Additive | Microcrystalline cellulose | 25.00 |
|  | Total | 100.00 |

According to the prescription in table 13, components contained in the hot melt process were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 200 rpm. The resulting extrudate was cooled and crushed, then the crushed material was screened through 60 mesh sieve; adding additive microcrystalline cellulose was added according to the prescription, mixed, and the resulting mixture was filled into capsules.

Example 9

The specific prescription is shown in Table 14.

TABLE 14

|  | Component | Percentage (%) |
| --- | --- | --- |
| Component contained in the hot melt process | Lurasidone | 9.94 |
|  | soluplus | 49.69 |
|  | Citric acid monohydrate | 10.41 |
|  | Poloxamer | 4.96 |
| Additive | Mannitol | 25.00 |
|  | Total | 100.00 |

According to the prescription in table 14, components contained in the hot melt process were weighed, mixed completely, and then added into the feeder of hot melt extruder to extrude by hot melting, while the temperature of barrel was set at 115° C., 135° C., 150° C., 150° C., 150° C., 150° C., 150° C., 145° C. and screw speed was set at 200 rpm. The resulting extrudate was cooled and crushed, then the crushed material was screened through 60 mesh sieve; additive mannitol was added according to the prescription, mixed, and the resulting mixture was filled into capsules.

Example 10

The specific prescription is shown in Table 15.

TABLE 15

|  | Component | Percentage (%) |
| --- | --- | --- |
| Component contained in the hot melt process | Lurasidone | 9.94 |
|  | Soluplus | 49.69 |
|  | Fumaric acid | 10.41 |
|  | Poloxamer | 4.96 |
| Additive | Mannitol | 25.00 |
|  | Total | 100.00 |

According to the prescription in table 15, components contained in the hot melt process were weighed, mixed completely, and then added into the feeder of hot melt extruder to extrude by hot melting, while the temperature of barrel was set at 115° C., 135° C., 150° C., 150° C., 150° C., 150° C., 150° C., 145° C. and screw speed was set at 30 rpm. The resulting extrudate was cooled and crushed, then the crushed material was screened through 60 mesh sieve; additive mannitol was added according to the prescription, mixed, and the resulting mixture was filled into capsules.

Example 11

The specific prescription is shown in Table 16.

TABLE 16

|  | Component | Percentage (%) |
| --- | --- | --- |
| Component contained in the hot melt process | Lurasidone | 10.64 |
|  | Soluplus | 53.21 |
|  | Succinic acid | 11.15 |
| Additive | Mannitol | 25.00 |
|  | Total | 100.00 |

According to the prescription in table 16, components contained in the hot melt process were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 100 rpm. The resulting extrudate was cooled and crushed, then the crushed material was screened through 60 mesh sieve; additive mannitol was added according to the prescription, mixed, and the resulting mixture was filled into capsules.

Example 12

The specific prescription is shown in Table 17.

TABLE 17

|  | Component | Percentage (%) |
| --- | --- | --- |
| Component contained in the hot melt process | Lurasidone | 8.94 |
|  | Soluplus | 44.70 |
|  | Citric acid monohydrate | 9.36 |
|  | Fumaric acid | 12.00 |
| Additive | Mannitol | 25.00 |
|  | Total | 100.00 |

According to the prescription in table 17, components contained in the hot melt process were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 200 rpm. The resulting extrudate was cooled and crushed, then the crushed material was screened through 60 mesh sieve; adding additive mannitol was added according to the prescription, mixed, and the resulting mixture was filled into capsules.

Example 13

The specific prescription is shown in Table 18.

TABLE 18

|  | Component | Percentage (%) |
|---|---|---|
| Component contained in the hot melt process | Lurasidone | 1.42 |
|  | Soluplus | 70.75 |
|  | Citric acid monohydrate | 2.83 |
| Additive | Mannitol | 25.00 |
|  | Total | 100.00 |

According to the prescription in table 18, components contained in the hot melt process were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 300 rpm. The resulting extrudate was cooled and crushed, then the crushed material was screened through 60 mesh sieve; additive mannitol was added according to the prescription, mixed, and the resulting mixture was filled into capsules.

Example 14

The specific prescription is shown in Table 19.

TABLE 19

|  | Component | Percentage (%) |
|---|---|---|
| Component contained in the hot melt process | Lurasidone | 1.47 |
|  | Soluplus | 44.12 |
|  | Citric acid monohydrate | 29.41 |
| Additive | Mannitol | 25.00 |
|  | Total | 100.00 |

According to the prescription in table 19, components contained in the hot melt process were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 300 rpm. The resulting extrudate was cooled and crushed, then the crushed material was screened through 60 mesh sieve; additive mannitol was added according to the prescription, mixed, and the resulting mixture was filled into capsules.

Example 15

The specific prescription is shown in Table 20.

TABLE 20

|  | Component | Percentage (%) |
|---|---|---|
| Component contained in the hot melt process | Lurasidone | 24.61 |
|  | Soluplus | 24.61 |
|  | Citric acid monohydrate | 25.78 |
| Additive | Mannitol | 25.00 |
|  | Total | 100.00 |

According to the prescription in table 20, components contained in the hot melt processes were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 300 rpm. The resulting extrudate was cooled and crushed, then the crushed material was screened through 60 mesh sieve; additive mannitol was added according to the prescription, mixed, and the resulting mixture was filled into capsules.

Example 16

The specific prescription is shown in Table 21.

TABLE 21

|  | Component | Percentage (%) |
|---|---|---|
| Components contained in the hot melt process | Lurasidone | 10.34 |
|  | Soluplus | 51.69 |
|  | Citric acid monohydrate | 0.64 |
| Additive | Microcrystalline cellulose | 31.33 |
|  | Crospovidone | 5.00 |
|  | Magnesium stearate | 1.00 |
|  | Total | 100.00 |

According to the prescription in table 21, components contained in the hot melt processes were weighed, mixed completely, and then added into the feeder of hot melt extruder to extrude by hot melting, while the temperature of barrel was set at 115° C., 135° C., 165° C., 165° C., 165° C., 165° C., 165° C., 160° C. and screw speed was set at 300 rpm. The resulting extrudate was cooled and crushed, then the crushed material was screened through 60 mesh sieve; additives was added according to the prescription, mixed, and the resulting mixture was filled into capsules.

Based on the above comparative examples and preparation examples, the inventor conducted XRD examination (as described in Example 17) on the hot melt powder obtained from preparation examples, and in vitro dissolving experiments and pharmacokinetic experiments (as described in Examples 18 and 19) of the formulation prepared from the comparative examples and preparation examples were performed. The details are described in follows.

Example 17

In this embodiment, the inventor conducted XRD analysis of hot melt powder prepared in examples 1, 3, and 4 using an X-ray powder diffractometer. The instruments are manufactured by PANalytical B.V, type: Empyrean, the instrument parameters are shown in Table 22.

TABLE 22

| Project | parameter |
|---|---|
| X-ray | Cu, kα, Kα1 (Å): 1.540598; Kα2 (Å): 1.544426; Kα2/Kα1 intensity ratio: 0.50 |
| X-ray tube parameters setting | 45 kV, 40 mA |
| Divergence slit | Automatic, Irradiated length = 10.0 mm |
| Anti-scatter slit of launching | 1° |
| Anti-scatter slit of receiving | 6.6 mm |
| Monochromator | Nothing |
| Scan pattern | Reflection mode |
| Specimen holder | Monocrystalline silicon |
| Scan mode | Continuous |
| Scan range (°2TH) | 3°~40° |
| Scanning step (°2TH) | 0.0167° |
| scanning speed s/step | 10 |

Taking appropriate amount of the test sample, and the zerobackground sample was racked in a circular box and pressed with a glass slide gently to get a flat surface, and fixed with a zero-background sample holder. After the instrument had run stably, the instrument scanned one time according to the test conditions shown in table 22 and the spectrum was recorded. The specific test results were shown in FIGS. 1 to 3.

Figure 1:
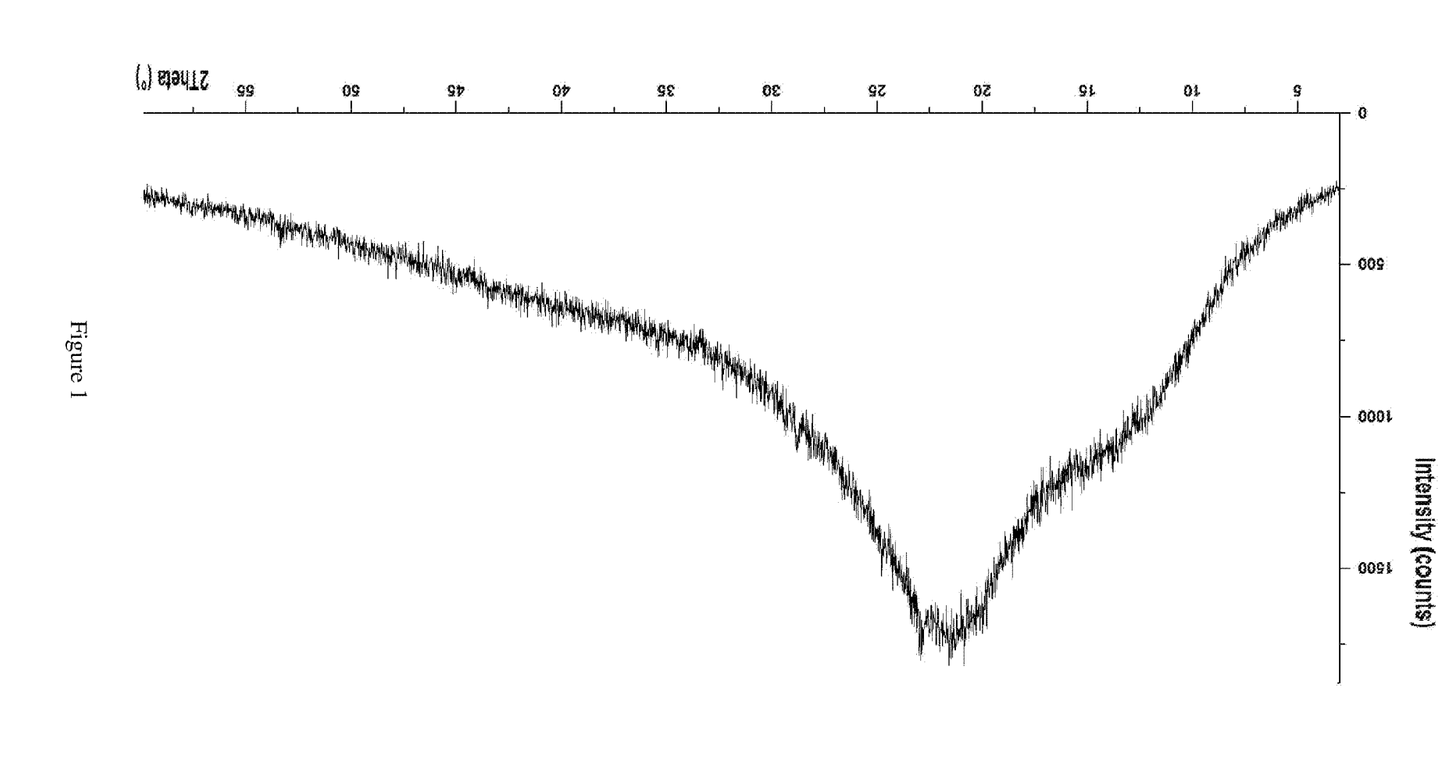
FIG. 1 shows an XRD pattern of hot melt powder prepared in example 17 of the invention.
Figure 2:
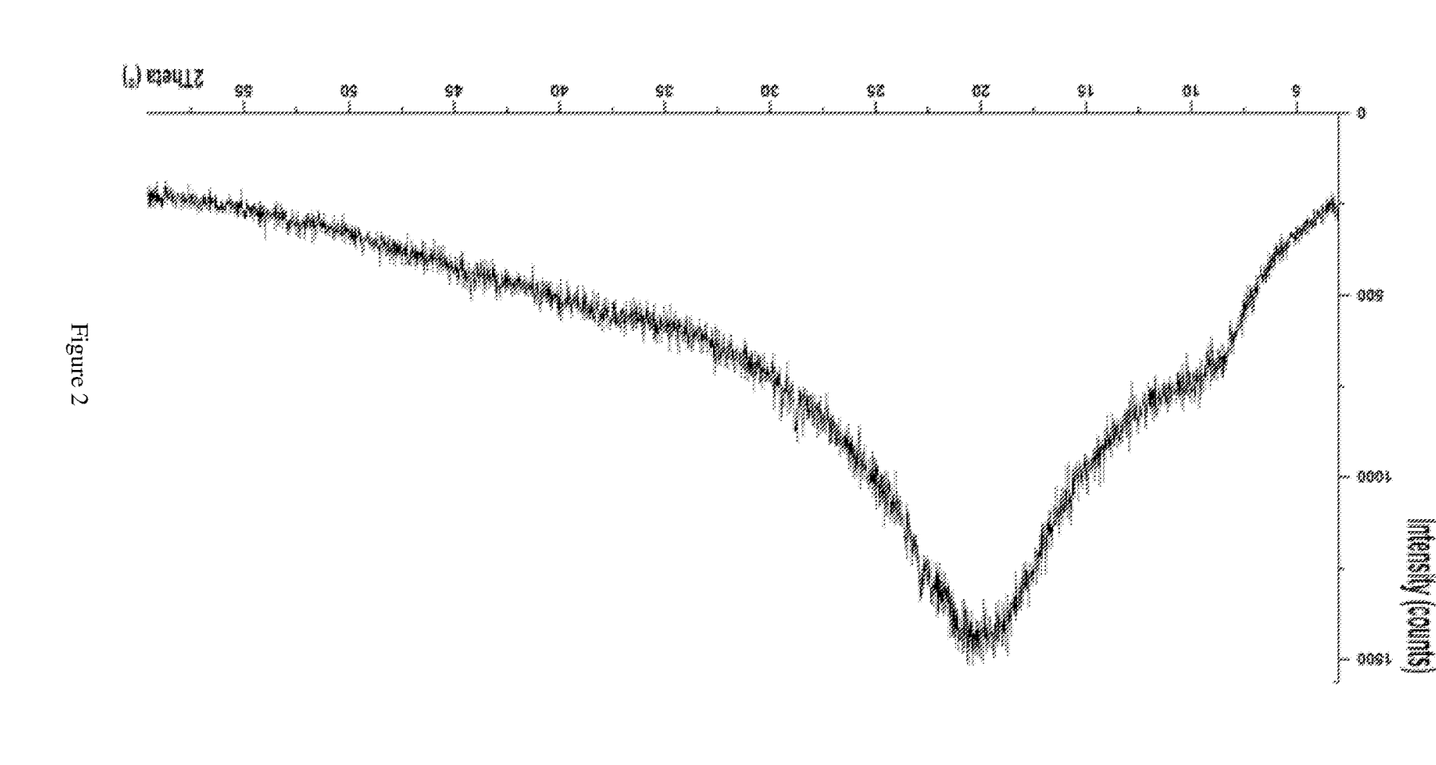
FIG. 2 shows an XRD pattern of hot melt powder prepared in example 17 of the invention.
Figure 3:
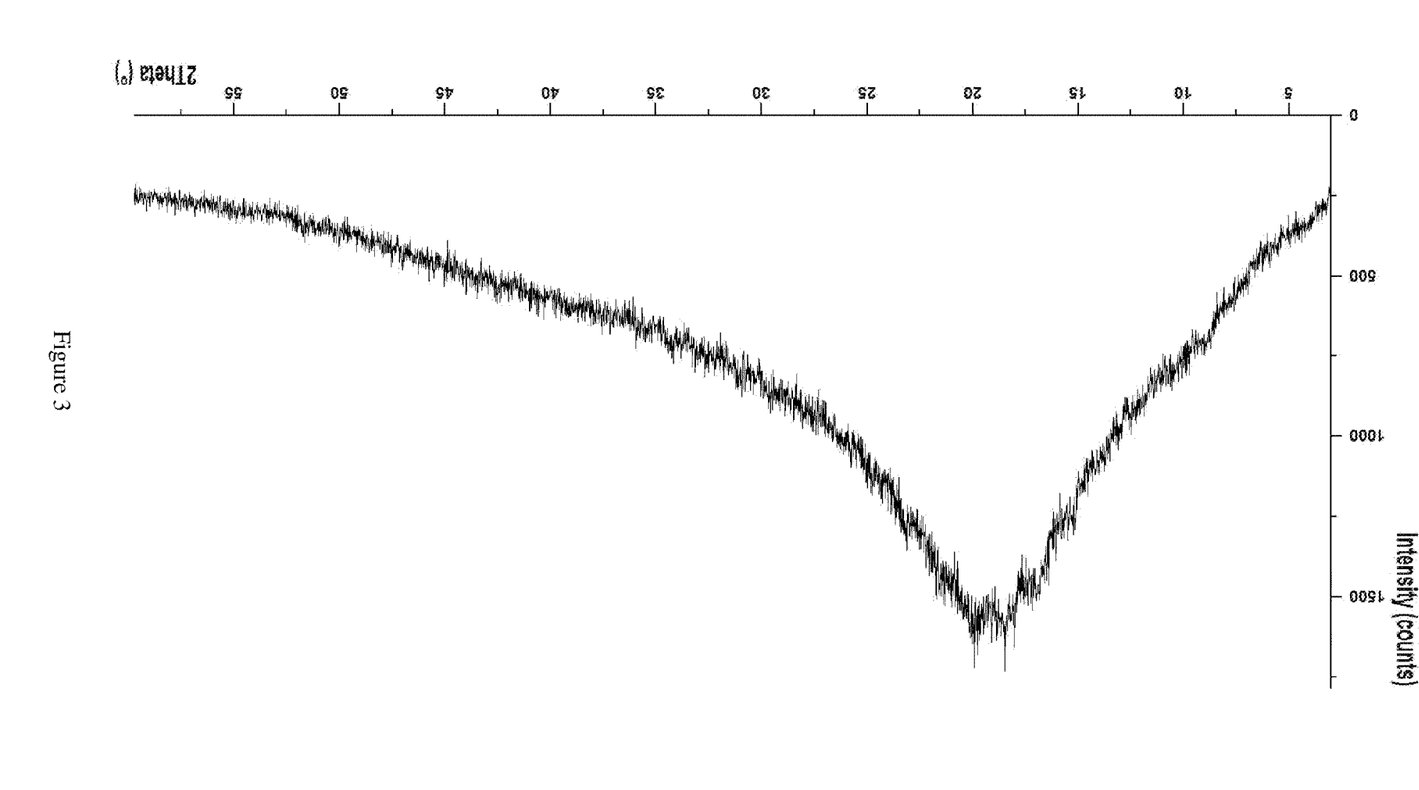
FIG. 3 shows an XRD pattern of hot melt powder prepared in example 17 of the invention.

As can be seen from FIGS. 1 to 3, the hot-melt powders prepared in examples 1, 3 and 4 were amorphous.

Example 18 In Vitro Dissolution Test

In this example, the reference formulation (lurasidone hydrochloride tablet, 40 mg, Sumitomo), capsules of comparative examples 1 to 6 and composition of examples 1 to 16 in vitro dissolution tests were performed in a simulation upper intestinal liquid medium (pH 6.0 buffer containing 0.01% SDS) under an in-line filter condition, the medium volume was 900±9 mL, the medium temperature was 37.0±0.5° C., a paddle method was adopted with 50 rpm. Sampling time points in dissolution test were 5 min, 10 min, 15 min, 20 min, 30 min, 45 min, 60 min, 150 rpm-15 min. Sampling position: the midpoint of the tip of the blade and the liquid surface, 10 mm away from the inner wall of the vessel. Dissolution medium (pH 6.0 buffer containing 0.01% SDS) preparation: 7.8 g of sodium dihydrogen phosphate dihydrate and 0.224 g of sodium hydroxide were weighed, and 1000 mL of water was added to dissolve and mix them uniformly. pH value was adjusted to 6.00±0.05 with saturated sodium hydroxide solution or phosphoric acid; 0.1 g SDS was weighed and added into the above buffer solution; the components in the resulting mixture were dissolved by heating slightly and the mixture was stirred uniformly to give the desired dissolution medium. The HPLC method was used for the determination of content of in vitro dissolution. The experimental conditions were as follows: HPLC instrument model: Agilent 1260; chromatographic conditions: column: Kromasil 100-5 C18 4.6×50 mm, 5 μm; column temperature: 30° C.; wavelength: 230 nm; flow rate: 1.0 mL/min; injection volume: 20 μL; run time: 4.5 min (main peak RT≈2 min); mobile phase: 0.05 mol/L phosphate buffer (pH 3.0): acetonenitrile (6:4) (V:V, volume ratio). Specifically, preparation method of 0.05 mol/L disodium hydrogen phosphate solution (pH 3.0) was described as follows: 7.098 g of disodium hydrogen phosphate was weighed, and 1000 mL of purified water was added to dissolve the disodium hydrogen phosphate; the pH value was adjusted with phosphoric acid to 3.0±0.05, the components in the resulting mixture were mixed uniformly and then the mixture was filtered through filter membrane (polyethersulfone, 0.45 μm, 0=50 mm, jin Teng) by suction. Mobile phase: 0.05 mol/L disodium hydrogen phosphate solution (pH 3.0) and acetonitrile having a volume ratio of 6:4 was mixed uniformly, and the resulting mixture was degassed for 15 min by ultrasonic to give the desired mobile phase.

The results were shown in table 23.

Table 23 dissolution of each of the comparative examples and examples in pH 6.0 buffer containing 0.01% SDS (n = 3)

| Test number | 5 min | 10 min | 15 min | 20 min | 30 min | 45 min | 60 min | 150 rpm-15 min |
|---|---|---|---|---|---|---|---|---|
| Reference formulation | 0 ± 0.00 | 1 ± 0.58 | 2 ± 0.00 | 2 ± 0.00 | 2 ± 0.00 | 2 ± 0.58 | 2 ± 0.58 | — |
| Comparative example 1 | 0 ± 0.04 | 1 ± 0.25 | 1 ± 0.23 | 1 ± 0.32 | 1 ± 0.36 | 2 ± 0.45 | 2 ± 0.34 | 3 ± 0.76 |
| Comparative example 2 | — | 0 ± 0.04 | 1 ± 0.11 | 1 ± 0.07 | 1 ± 0.11 | 1 ± 0.10 | 1 ± 0.03 | 2 ± 0.04 |
| Comparative example 3 | — | 1 ± 0.17 | 3 ± 1.25 | 5 ± 2.97 | 6 ± 1.15 | 7 ± 1.02 | 7 ± 0.30 | 7 ± 0.13 |
| Comparative example 4 | 0 ± 0.02 | 0 ± 0.04 | 0 ± 0.06 | 0 ± 0.03 | 0 ± 0.06 | 0 ± 0.05 | 0 ± 0.07 | 0 ± 0.13 |
| Comparative example 5 | 0 ± 0.00 | 1 ± 0.58 | 1 ± 0.58 | 2 ± 1.15 | 2 ± 0.58 | — | 2 ± 0.58 | 4 ± 1.00 |
| Comparative example 6 | 0 ± 0.58 | 3 ± 0.58 | 4 ± 0.58 | 5 ± 0.58 | 5 ± 0.58 | — | 6 ± 0.58 | 8 ± 0.58 |
| Example 1 | 5 ± 3.74 | 14 ± 5.76 | 19 ± 4.48 | 24 ± 7.53 | 27 ± 8.58 | 30 ± 8.20 | 30 ± 7.40 | 28 ± 6.03 |
| Example 3 | 5 ± 1.17 | 20 ± 2.51 | 24 ± 2.46 | 25 ± 2.75 | 24 ± 0.83 | 21 ± 1.04 | 23 ± 1.48 | 29 ± 3.42 |
| Example 4 | 18 ± 5.76 | 44 ± 3.90 | 49 ± 3.00 | 74 ± 2.08 | 72 ± 2.69 | 65 ± 9.67 | 64 ± 2.67 | 69 ± 3.62 |
| Example 5 | 17 ± 5.13 | 40 ± 5.45 | 45 ± 6.59 | 47 ± 11.40 | 40 ± 6.89 | 39 ± 11.69 | — | 60 ± 5.04 |
| Example 6 | 6 ± 4.77 | 6 ± 4.29 | 15 ± 4.60 | 23 ± 6.81 | 31 ± 8.26 | 30 ± 11.05 | 26 ± 11.15 | 23 ± 11.16 |
| Example 7 | 0 ± 0.00 | 1 ± 0.32 | 2 ± 0.56 | 3 ± 1.01 | 4 ± 1.30 | 7 ± 1.32 | 8 ± 0.56 | 26 ± 4.58 |
| Example 8 | 1 ± 0.75 | 7 ± 1.96 | 14 ± 3.33 | 18 ± 4.26 | 25 ± 3.50 | 27 ± 3.65 | 30 ± 2.52 | 30 ± 2.46 |
| Example 9 | 10 ± 7.98 | 27 ± 10.72 | 37 ± 9.96 | 44 ± 9.68 | 52 ± 8.84 | 59 ± 4.54 | 62 ± 2.54 | 61 ± 10.85 |
| Example 10 | 8 ± 3.08 | 22 ± 4.26 | 38 ± 4.04 | 45 ± 1.06 | 49 ± 1.18 | 53 ± 1.72 | 55 ± 0.98 | 61 ± 2.05 |
| Example 11 | 4 ± 0.56 | 14 ± 0.68 | 20 ± 1.93 | 24 ± 2.38 | 26 ± 3.00 | 26 ± 2.93 | 28 ± 3.44 | 24 ± 1.51 |
| Example 12 | 3 ± 1.25 | 12 ± 3.45 | 20 ± 4.53 | 24 ± 4.10 | 31 ± 6.33 | 41 ± 12.68 | 52 ± 16.47 | — |
| Example 13 | 3 ± 1.43 | 10 ± 3.57 | 16 ± 3.81 | 21 ± 4.22 | 26 ± 2.32 | 29 ± 2.48 | 30 ± 1.21 | 37 ± 1.24 |
| Example 14 | 3 ± 1.83 | 13 ± 2.74 | 21 ± 3.08 | 25 ± 2.44 | 29 ± 2.90 | 33 ± 3.03 | 35 ± 2.49 | 34 ± 0.73 |
| Example 15 | 1 ± 0.33 | 4 ± 0.86 | 7 ± 1.79 | 9 ± 1.25 | 13 ± 1.57 | 14 ± 2.26 | 20 ± 5.64 | 33 ± 6.21 |
| Example 16 | 2 ± 0.63 | 9 ± 0.65 | 14 ± 0.76 | 17 ± 0.57 | 19 ± 1.00 | 22 ± 2.34 | 28 ± 2.75 | 39 ± 3.27 |

It can be seen from the dissolution results in table 23 that the dissolution quantities of reference formulation, samples in comparative examples 1, 2, 3 and 4 in pH 6.0 buffer containing 0.01% SDS were extremely low to 7%; the dissolution quantities of samples in comparative examples 5 and 6 which were prepared by simple physical mixing were slightly increased, with only 4% and 8% respectively. At the same time, the inventor found that the dissolution of the comparative example using a non-hot melting process was only slightly improved. Therefore, the inventor concludes that the dissolution quantities of the drugs prepared in the comparative examples 1 to 3 in the small intestine are very low and affect the absorption of the drug in the small intestine; and the dissolution quantities of the drug prepared in the comparative examples 4 to 6 in the small intestine increase slightly but not significantly. Compared with the reference formulation and the comparative examples, the dissolution quantities of lurasidone in examples 1 to 16 are significantly increased, which significantly increases the dissolution rate of the drug and greatly reduce the risk of precipitation of the drug in the small intestine which has been dissolved in the stomach. Compositions in examples 1 to 16 are very favorable for the absorption of the drug in the small intestine.

Example 19 Pharmacokinetic Experiments

In this example, the inventor took the compositions obtained from example 1 and example 2 as examples, conducted the beagle dog pharmacokinetic test of the tablets of the reference formulation and the capsules of example 1 and example 2, each group n=3, respectively, to investigate the effect of food on their pharmacokinetics under fasted or fed conditions. LC-MS-MS was used to detect the content of lurasidone in beagle dog's plasma. Pharmacokinetic parameters were calculated by non-compartmental model with WinNonlin 6.3 software. The results were shown in table 24.

TABLE 24

| | | | | | | |
|---|---|---|---|---|---|---|
| pharmacokinetic parameters in Fasted and Fed Dogs | | | | | | |
| | Project | Time to peak $T_{max}$ (hours) | Peak blood concentration $C_{max}$ (ng/mL) | 0-t Area under the curve $AU_{Clast}$ (h * ng/mL) | 0-∞ Area under the curve $AUC_{inf}$ (h * ng/mL) | half-life period $T_{1/2}$ (hours) |
| Reference formulation, fasted | Mean ± SD | 0.917 ± 0.95 | 57.3 ± 43 | 115 ± 68 | 127 ± 72 | 6.98 ± 2.3 |
| Reference formulation, fed | Mean ± SD | 3.67 ± 5.5 | 125 ± 90 | 282 ± 71 | 340 ± 59 | 17.2 ± 10 |
| Example 1, fasted | Mean ± SD | 0.667 ± 0.29 | 291 ± 66 | 458 ± 230 | 480 ± 240 | 2.66 ± 0.68 |
| Example 1, fed | Mean ± SD | 1.83 ± 1.90 | 258 ± 110 | 613 ± 120 | 631 ± 130 | 1.92 ± 0.66 |
| Example 2, fasted | Mean ± SD | 1.5 ± 0.87 | 227 ± 140 | 376 ± 88 | 393 ± 93 | 4.95 ± 3 |
| Example 2, fed | Mean ± SD | 3.5 ± 2.8 | 173 ± 150 | 444 ± 45 | 461 ± 54 | 3.45 ± 2.6 |

As can be seen in table 24, after administrating the reference formulation to beagle by oral under fasted or fed conditions, $AUC_{inf}$ and $C_{max}$ of lurasidone in beagle had great difference because of food, $AUC_{inf}$ value under fed conditions was 2.68 fold of $AUC_{inf}$ value under fasted conditions, whereas $C_{max}$ value under fed conditions was 2.18-fold of $C_{max}$ value under fasted conditions. The food effect is very obvious. While the $AUC_{inf}$ value under fed conditions in example 1 was 1.3-fold of the $AUC_{inf}$ value under fasted conditions, and the $C_{max}$ value under fed conditions was 0.89-fold of the $C_{max}$ value under fasted conditions; the $AUC_{inf}$ value under fed conditions in example 2 was 1.17-fold of the $AUC_{inf}$ value under fasted conditions, and the $C_{max}$ value under fed conditions was 0.76-fold of the $C_{max}$ value under fasted conditions; the bioavailabilities of examples 1 and 2 were also improved as compared with the reference formulation. The food effects in both groups were significantly reduced.

In conclusion, the hot melt formulation of lurasidone disclosed herein is advantageous to the absorption of lurasidone and can ensure the increase of lurasidone dissolution in small intestine without considering the influence of food on the absorption of lurasidone, reduces the excessive medication restrictions and avoids reduced efficacy due to improper medication or even invalid, ensures the normal efficacy of drug, thereby increases the patient's medication flexibility and compliance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A lurasidone solid dispersion comprising lurasidone, a medicinal hot melt carrier and an acidic regulator, wherein the lurasidone is in a form of free base, and wherein the medicinal hot melt carrier is polyvinyl caprolactam-polyvinyl acetate-polyethylene glycol graft copolymer.

2. The lurasidone solid dispersion according to claim 1, wherein a weight ratio of the lurasidone to the medicinal hot melt carrier is ranged from about 1:1 to about 1:50,
wherein a weight ratio of the lurasidone to the acidic regulator is ranged from about 1:0.05 to about 1:25, and
wherein the acidic regulator comprises at least one of citric acid monohydrate, anhydrous citric acid, fumaric acid, malic acid, succinic acid, ascorbic acid, tartaric acid, sorbic acid and glycine.

3. The lurasidone solid dispersion according to claim 1, wherein the lurasidone solid dispersion further comprises a plasticizer,
wherein a weight ratio of the lurasidone to the plasticizer is ranged from about 1:0 to about 1:10, and
wherein the plasticizer comprises at least one of a poloxamer, a polyethylene glycol, triethyl citrate, diethyl phthalate, and glycerol monostearate.

4. A method of preparing a lurasidone solid dispersion comprising:
(a) melting and mixing a mixture containing lurasidone and a medicinal hot melt carrier; and
(b) cooling the mixture to give the lurasidone solid dispersion,
wherein the lurasidone is in a form of free base, and wherein the medicinal hot melt carrier is polyvinyl caprolactam-polyvinyl acetate-polyethylene glycol graft copolymer.

5. A method of preparing a lurasidone solid dispersion comprising:
(a) melting and mixing a mixture containing lurasidone, a medicinal hot melt carrier, an acidic regulator, and optionally a plasticizer; and
(b) cooling the mixture to give the lurasidone solid dispersion,
wherein the lurasidone is in a form of free base, and wherein the medicinal hot melt carrier comprises is polyvinyl caprolactam-polyvinyl acetate-polyethylene glycol graft copolymer.

6. The method according to claim 4, wherein the melting and mixing step is carried out in a hot melt extruder.

7. The method according to claim 4, wherein a weight ratio of the lurasidone to the medicinal hot melt carrier is ranged from about 1:1 to about 1:50.

8. The method according to claim 5, wherein a weight ratio of the lurasidone to the acidic regulator is ranged from about 1:0.05 to about 1:25, and
wherein the acidic regulator comprises at least one of citric acid, fumaric acid, malic acid, succinic acid, ascorbic acid, tartaric acid, sorbic acid and glycine.

9. The method according to claim 4, wherein the mixture further comprises a plasticizer,
wherein a weight ratio of the lurasidone to the plasticizer is ranged from about 1:0 to about 1:10, and
wherein the plasticizer comprises at least one of a poloxamer, a polyethylene glycol, triethyl citrate, diethyl phthalate and glycerol monostearate.

10. The method according to claim 6, wherein the melting and mixing step is carried out at a temperature from about 80° C. to about 200° C. while the screw speed of the hot melt extruder is from about 30 rpm to about 1000 rpm.

11. The method according to claim 6, wherein the melting and mixing step is carried out at a temperature from about 115° C. to about 175° C. while the screw speed of the hot melt extruder is from about 30 rpm to about 300 rpm.

12. A lurasidone solid dispersion prepared by the method according to claim 4.

13. A pharmaceutical composition comprising the lurasidone solid dispersion according to claim 1,
wherein the pharmaceutical composition further comprises a pharmaceutically acceptable excipient;
wherein the pharmaceutically acceptable excipient comprises at least one of a filler, a disintegrant, an adhesive, a surfactant, a flavoring agent and a lubricant;
wherein the filler comprises at least one of lactose, starch, microcrystalline cellulose, mannitol, dextrin, pregelatinized starch, corn starch, sorbitol, calcium sulfate, calcium hydrogen phosphate and calcium carbonate;
wherein the disintegrant comprises at least one of crospovidone, croscarmellose sodium, sodium starch glycolate, dry starch and low-substituted hydroxypropyl cellulose;
wherein the adhesive comprises at least one of starch, pregelatinized starch, sodium carboxymethyl cellulose, hydroxypropyl cellulose, methyl cellulose, ethyl cellulose, hypromellose, sucrose, gelatin, polyvinylpyrrolidone, microcrystalline cellulose and copovidone;
wherein the surfactant comprises at least one of sodium lauryl sulfate, quaternary ammonium compound, lecithin, fatty acid glycerides, sorbitan fatty acid ester and polysorbate;
wherein the flavoring agent comprises at least one of sucrose, sucralose, acesulfame, aspartame, stevioside, sodium saccharin and sodium cyclamate;
wherein the lubricant comprises at least one of magnesium stearate, colloidal silicon dioxide, stearic acid, talc, glyceryl behenate, hydrogenated castor oil, sodium stearyl fumarate; and
wherein the pharmaceutical composition is in a form of granule, tablet, capsule or enteric-coated preparation.

14. A pharmaceutical combination characterized in that the pharmaceutical combination is for use in treating a mental disease, comprising:
lurasidone used as a first active agent, wherein the lurasidone exists in a form of lurasidone solid dispersion according to claim 1; and
a medicament different from lurasidone used as a second active agent, wherein the medicament is used for treating the mental disease, and wherein the mental disease is schizophrenia or type I bipolar affective disorder.

15. A method of treating a mental disease in a patient, comprising administering to the patient a therapeutically effective amount of the lurasidone solid dispersion according to claim 12, wherein the mental disease is schizophrenia or type I bipolar affective disorder.

16. The method according to claim 5, wherein the melting and mixing step is carried out in a hot melt extruder.

17. The method according to claim 5, wherein a weight ratio of the lurasidone to the medicinal hot melt carrier is ranged from about 1:1 to about 1:50.

18. A lurasidone solid dispersion prepared by the method according to claim 5.

19. A pharmaceutical composition comprising the lurasidone solid dispersion according to claim 12,
wherein the pharmaceutical composition further comprises a pharmaceutically acceptable excipient;

wherein the pharmaceutically acceptable excipient comprises at least one of a filler, a disintegrant, an adhesive, a surfactant, a flavoring agent and a lubricant;

wherein the filler comprises at least one of lactose, starch, microcrystalline cellulose, mannitol, dextrin, pregelatinized starch, corn starch, sorbitol, calcium sulfate, calcium hydrogen phosphate and calcium carbonate;

wherein the disintegrant comprises at least one of crospovidone, croscarmellose sodium, sodium starch glycolate, dry starch and low-substituted hydroxypropyl cellulose;

wherein the adhesive comprises at least one of starch, pregelatinized starch, sodium carboxymethylcellulose, hydroxypropyl cellulose, methyl cellulose, ethyl cellulose, hypromellose, sucrose, gelatin, polyvinylpyrrolidone, microcrystalline cellulose and copovidone;

wherein the surfactant comprises at least one of sodium lauryl sulfate, quaternary ammonium compound, lecithin, fatty acid glycerides, sorbitan fatty acid ester and polysorbate;

wherein the flavoring agent comprises at least one of sucrose, sucralose, acesulfame, aspartame, stevioside, sodium saccharin and sodium cyclamate;

wherein the lubricant comprises at least one of magnesium stearate, colloidal silicon dioxide, stearic acid, talc, glyceryl behenate, hydrogenated castor oil, sodium stearyl fumarate; and wherein the pharmaceutical composition is in a form of granule, tablet, capsule or enteric-coated preparation.

20. A pharmaceutical combination characterized in that the pharmaceutical combination is for use in treating a mental disease, comprising:

lurasidone used as a first active agent, wherein the lurasidone exists in a form of lurasidone solid dispersion according to claim 12; and a medicament different from lurasidone used as a second active agent, wherein the medicament is used for treating the mental disease, and wherein the mental disease is schizophrenia or type I bipolar affective disorder.

21. A method of treating a mental disease in a patient, comprising administering to the patient a therapeutically effective amount of the pharmaceutical composition according to claim 13, wherein the mental disease is schizophrenia or type I bipolar affective disorder.

* * * * *